United States Patent [19]

Feldman

[11] Patent Number: 4,964,859
[45] Date of Patent: Oct. 23, 1990

[54] DIAPER WITH INTEGRAL CHANGING PAD AND DISPOSAL CONTAINER

[76] Inventor: Ruth L. Feldman, c/o Dr. Robert Plotkin, 28 Brenan Dr., Bryn Mawr, Pa. 19010

[21] Appl. No.: 386,572

[22] Filed: Jul. 28, 1989

[51] Int. Cl.$^5$ ............................................. A61F 13/16
[52] U.S. Cl. ................................. 604/385.1; 206/223; 206/440
[58] Field of Search .................. 604/385.1, 385.2, 361; 206/223, 440

[56] References Cited

U.S. PATENT DOCUMENTS

| | | | |
|---|---|---|---|
| 2,989,753 | 6/1961 | Burner | 604/385.1 |
| 4,085,753 | 4/1978 | Gellert | 604/385.1 |
| 4,738,677 | 4/1988 | Foreman | 604/385 R |
| 4,738,678 | 4/1988 | Paulis | 604/385 R |
| 4,743,240 | 5/1988 | Powell | 604/385 R |
| 4,781,712 | 11/1988 | Barabino et al. | 604/385.1 |
| 4,790,840 | 12/1988 | Cortina | 604/385.1 |
| 4,808,175 | 2/1989 | Hansen | 604/385 R |

*Primary Examiner*—J. L. Kruter
*Attorney, Agent, or Firm*—Robert G. Rosenthal

[57] ABSTRACT

A disposable diaper with an integral changing pad and disposal container forming an integrated changing system for an infant or incontinent adult is disclosed. The disposable diaper has a skin contacting moisture absorbing inner surface and a waterproof environment interfacing outer surface. A changing pad and disposal container is mounted to the outer surface of the diaper and includes a liquid impermeable membrane formed so as to define a closable pocket for retaining a towelette therein in the moistened state. At such time as the towelette is needed for wiping the skin, the pocket is expandable to form a disposal container for the soiled diaper and the spent towelette. A moist towelette is adapted to be stored within the changing pad and disposal container.

11 Claims, 4 Drawing Sheets

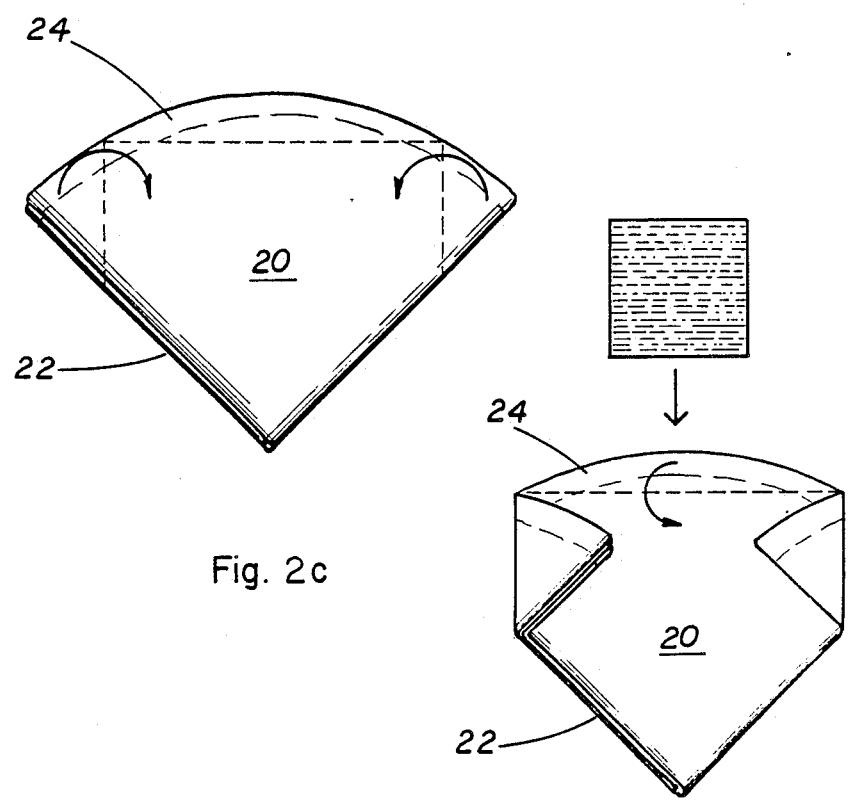
Fig. 2c
Fig. 2d
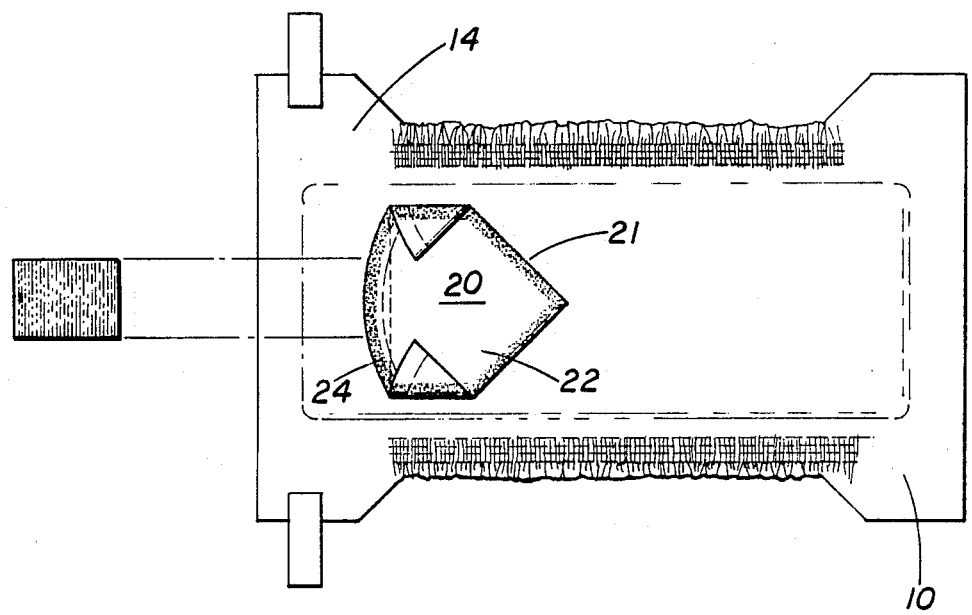
Fig. 3

4,964,859

DIAPER WITH INTEGRAL CHANGING PAD AND DISPOSAL CONTAINER

FIELD OF THE INVENTION

This invention relates generally to the field of disposable diapers and more specifically to the field of diapers that include an integral wiping cloth and disposal container.

BACKGROUND OF THE INVENTION

Disposal diapers are well known as are changing pads, moistened towelettes and disposal bags. Whether diapering an infant or an incontinent adult, these articles become bulky and burdensome to store, transport, and replace. Even under the best of conditions, when all the necessary items are on hand, developmental and environmental factors such as the lack of a clean, safe changing area and the mobility (or lack thereof) of an infant or adult, can reduce the speed, sanitation and convenience in the diapering process. In addition, the mobility of the individual being diapered as well as the number of others requiring diapering in the same environment can induce additional physical strain on the caretaker. Any streamlining of the diapering process must, therefore, place a premium on speed, convenience and sanitation.

In view of the foregoing, it is an object of the present invention to provide a changing system which is sanitary.

It is another object of the present invention to provide a changing system which is easily transportable and is compact.

It is still another object of the present invention to provide a changing system which is easily disposable.

It is yet another object of the present invention to provide a changing system which includes all of the necessities required to change a baby in a single item.

It is yet another object of the present invention to provide a changing system that reduces physical and emotional strain on the caregiver.

SUMMARY OF THE INVENTION

In accordance with the present invention, there is provided a disposable diaper, changing pad and disposal container forming a integrated baby changing system. The disposable diaper has a skin contacting moisture absorbing inner surface and a waterproof environment interfacing outer surface. A changing pad and disposal container means is mounted to the outer surface of the diaper and includes a liquid impermeable membrane formed so as to define a closable pocket for retaining a towelette therein in the moistened state until such time as the towelette is needed for wiping the skin. The pocket is expandable to form a changing pad and then after cleansing, a disposal container for the soiled diaper and the spent towelette. A moist towelette is adapted to be stored within the changing pad and disposal container means.

BRIEF DESCRIPTION OF THE DRAWINGS

Some of the objects of the invention having been stated, other objects will appear as the description proceeds when taken in connection with the accompanying drawings in which:

FIG. 2c is a plan view showing the cone being folded into a pocket.

FIG. 2d is a plan view of the completed pocket.

FIG. 3 is a plan view of a diaper with the changing pad and disposal container means being connected thereto and the moistened towelette being inserted therein.

DETAILED DESCRIPTION OF THE ILLUSTRATED EMBODIMENT

While the present invention will be described more fully hereinafter, it is to be understood at the outset that persons of skill in the art may modify the invention herein described while still achieving the favorable results of the invention. Accordingly, the description which follows is to be understood as a broad teaching disclosure directed to persons of skill in the appropriate arts, and not as limiting upon the present invention.

Figure 1:
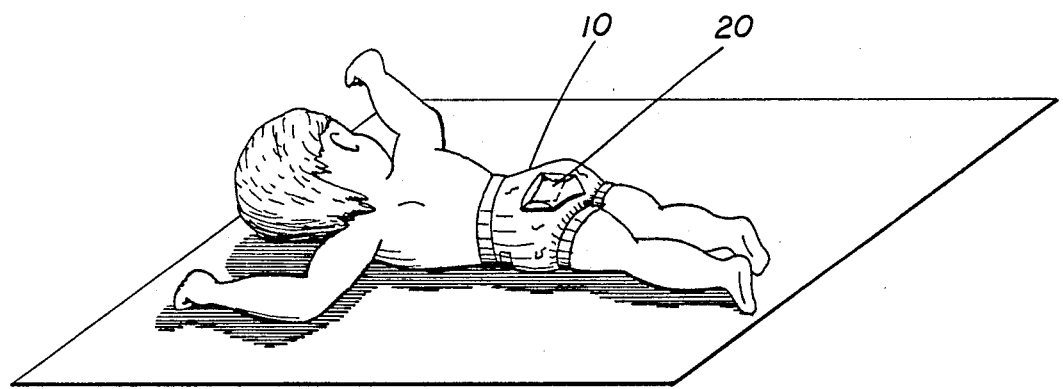
FIG. 1 is a perspective view of a child wearing the baby changing system of the present invention.

Referring more specifically to the drawings, and particularly to FIG. 1, the baby changing system is shown being worn by an infant. However, the reader will note that the present invention may employ with equal efficacy to incontinent adults. In general, a diaper 10 of conventional construction is employed. The diaper to includes a skin contacting moisture absorbing inner surface 12 and a waterproof environment interfacing outer surface 14 with a moisture absorbing material sandwiched therebetween.

Figure 4:
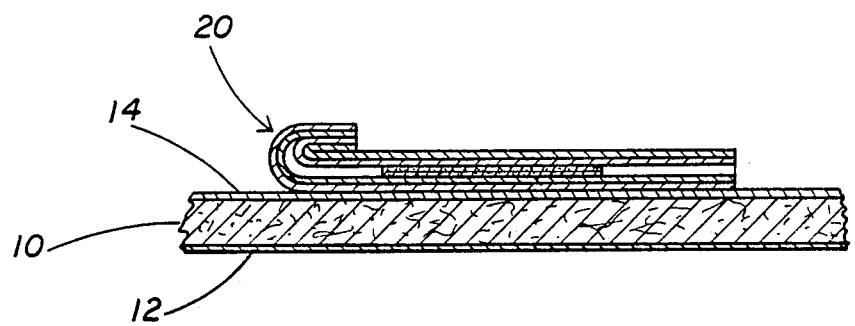
FIG. 4 is a side view taken in section of the diaper with the completed pocket connected thereto and housing the moistened towelette.
Figure 5:
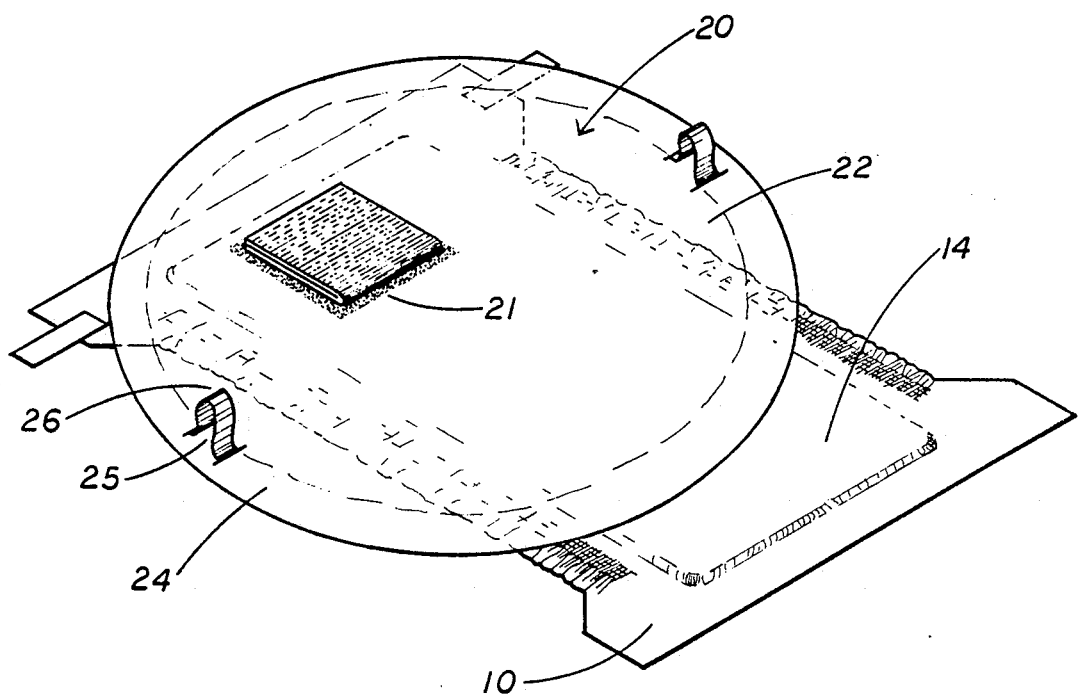
FIG. 5 is a perspective view showing the pocket opened with the towelette being positioned thereon.

As shown in FIGS. 3 through 5, a changing pad and disposal container means generally indicated at 20 is mounted via suitable means such as heat or pressure sealing to the outer surface of the diaper 10 (as best shown in FIG. 3). The changing pad and disposal container means 20 takes the form of a liquid impermeable membrane 22 which is formed into a sealable pocket for retaining a towelette therein in the moistened state. Additionally, only the wipes themselves may be enclosed in a small waterproof pocket. When it is desired to use the towelette for wiping the skin, the pocket is opened and the towelette is removed therefrom. As shown in FIG. 5, the pocket expands and forms a portable and attached changing pad. When a drawstring is pulled the pad becomes a disposal container for the soiled diaper and the spent towelette as will be explained in detail hereinbelow.

The liquid impermeable membrane in the illustrated embodiment takes the form of a circular plastic disk and includes a hem 24 located proximate its outer peripheral edge. Of course, other shapes such as a rectangle, hourglass, oval, etc. may also be employed. A drawstring or string 26 is provided and is slidably mounted within the hem 24. The hem 24 also includes a pair of oppositely positioned cut out portions 25 for providing ease of access to the drawstring 26 which may also contain a scent or deodorant.

Figure 2A:
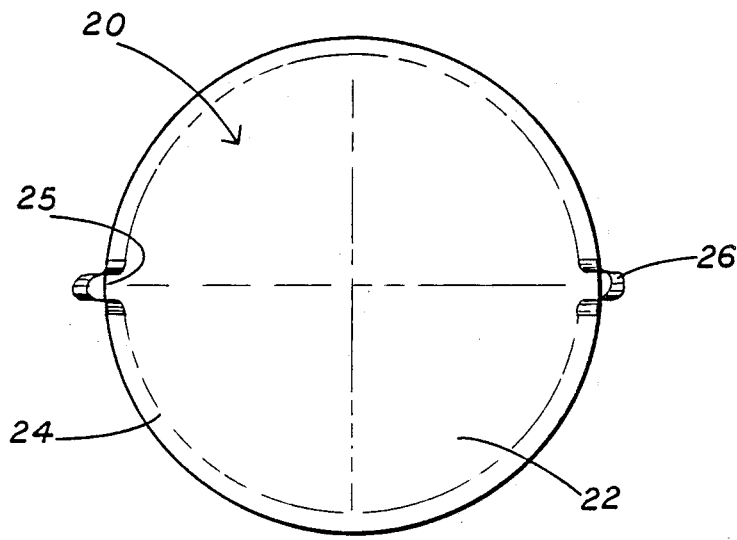
FIG. 2a is a plan view of the changing pad and disposal container means prior to being folded into a pocket.
Figure 2B:
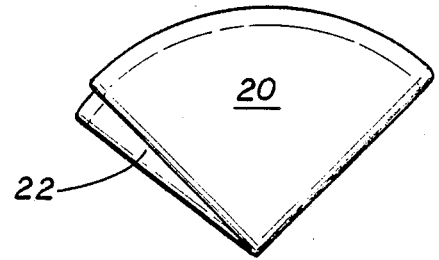
FIG. 2b is a plan view, taken in perspective of the changing pad and disposal container means being folded into a cone.

FIGS. 2through 2d illustrate the formation of the changing pad and disposal container means 20. First, a substantially circular plastic disk (FIG. 2a) is folded into a cone shape (FIG. 2b). Then the edges of the cone are folded inward and may be held in place by a suitable light adhesive or fusion process which will not interfere with the opening of the pocket. Next, the towelette is inserted into the pocket and finally, the top flap is folded down and is similarly held in place by a light adhesive (FIG. 2c). The completed pocket is illustrated in FIG. 2d. The edges of the cone may also be tucked inside forming pleats for a neater looking pocket. Similarly, when other membrane shapes are used, the shape of the pocket will change.

Figure 6:
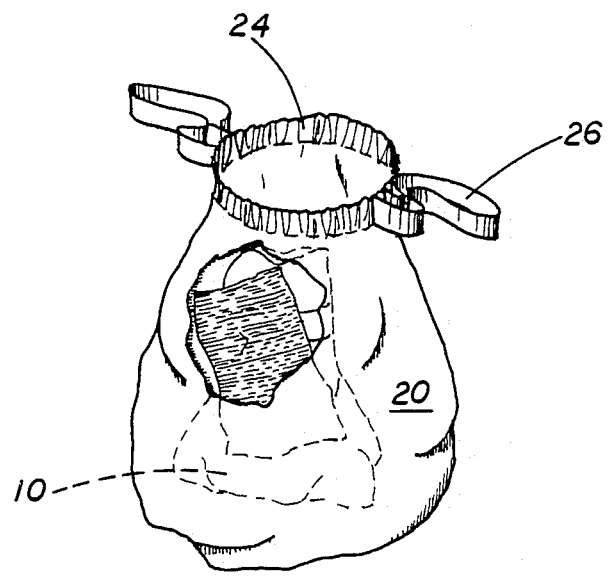
FIG. 6 is a perspective view of the changing pad and disposal container means inverted showing the spent diaper and used towelette stored therein.

In use, the changing pad and disposal container means 20 is secured to the outer surface 14 of the diaper 10 so as to overlie the child's buttox as shown in FIG. 1 until such time as the towelette is needed for wiping the skin. When the diaper becomes soiled, the caregiver unfolds the changing pad, removes the wipes and proceeds to position and change the child and upon completion, a disposal container is formed when the changing pad and disposal container means 20 is inverted and encircles the soiled diaper and the towelette. As best shown in FIG. 6, the entire package is then closed by pulling the drawstring 26.

It will be noted that the changing pad and disposal container means as shown in FIG. 2d may be employed as a diaper disposal and child clean-up system separate and apart from the diaper, and thus, may be sold individually. In addition, the pocket may contain a varying number of towelettes and the storage container means 20 may also include a visual indicator means, such as a colored adhesive-backed strip which may be used to close the pocket flap and which indicates the number of towelettes contained in the pocket. In this manner, the parent can choose an appropriate pocket depending on the extent to which the diaper may be soiled. Pockets sold in this manner will contain a suitable adhesive backing for attaching to the diaper.

In the drawings and specification, there has been set forth a preferred embodiment of the invention, and although specific terms are employed, they are used in a genuine and descriptive sense only and not for purposes of limitation.

That which is claimed is:

1. A disposable diaper, changing pad, and disposal container, forming an integrated changing system for infants or incontinent adults comprising:
    a disposable diaper having a skin contacting moisture absorbing inner surface and a waterproof environment interfacing outer surface;
    a changing pad and disposal container means mounted to the outer surface of said diaper, and comprising a liquid impermeable membrane folded to define a closable pocket for retaining a towelette therein in the moistened state until such time as the towelette is needed for wiping the skin, and said pocket being adapted to expand and to be unfolded to form a changing pad for use while diapering and upon completion of the diapering process to be used as a disposal bag for said soiled diaper and the spent towlette; and
    a moist towelette adapted to be stored within said changing pad and disposal container means.

2. The baby changing system according to claim 1 wherein said liquid impermeable membrane includes a closure means positioned proximate the outer peripheral edge of said changing pad and disposal means.

3. The changing system according to claim 2 wherein said changing pad and disposal container means comprises a substantially circular disk that includes a hem and wherein said closure means is slidably positioned within said hem.

4. The changing system of claim 1 wherein said changing pad and disposal container means is adapted to encircle and enclose the spent diaper.

5. The changing system of claim 2 wherein said closure means contains a deoderant to absorb odors from the spent diaper.

6. The changing system of claim 2 wherein said closure means comprises a string.

7. A disposable diaper, changing pad and disposal container forming an integrated changing system for infants or incontinent adults comprising:
    a disposable diaper having a skin contacitng moisture absorbing inner surface and a waterproof environment interfacing outer surface;
    a changing pad and disposal container means mounted to the outer surface of said diaper and comprising a liquid impermeable membrane in the form of a circular plastic disk folded into a cone and defining a closable pocket for retaining a towelette in the moistened state therein until such time as it is needed for wiping the skin, and said pocket being adapted to be expanded by unfolding and to form a changing pad for use during diapering and upon completion of the diapering process to be used as a disposal container for said soiled diaper and the spent towelette when inverted,
    a hem proximate the outer peripheral edge of said plastic disk;
    a closure means slidably positioned within said hem for closing said container means; and
    a moist towelette adapted to be stored within the changing pad and disposal container means, whereby the changing pad and disposal container means retains the towelette in the moistened state when the diaper is in use and is expandable to form a disposal container and to encircle spent diaper when inverted.

8. An attachment for a diaper of the type having a skin contacting moisture absorbing inner surface and a waterproof environment interfacing outer surface of the type which is commonly worn by infants or incontinent adults and comprising:
    a changing pad and disposal container means adapted to be mounted to the outer surface of said diaper and comprising a liquid impermeable memebrane formed so as to define a closed pocket and adapted to retain therein a towelette in the moistened state until such time as it is needed for wiping the skin, and said pocket being adapted to be opened and to expand to form a changing pad for use while diapering and upon completion of the diapering process to be used as a disposal container for the soiled diaper and the spent towelette,
    a moist towelette adapted to be stored within said changing pad and disposal container means.

9. An attachment for a diaper according to claim 8 further including adhesive means for attaching said changing pad and disposal container means to the outer surface of said diaper.

10. An attachment for a diaper according to claim 8 wherein said changing pad and disposal container means is adapted to receive a plurality of moist towelettes.

11. An attachment for a diaper according to claim 10 further including visual indicator means for indicating the number of towelettes contained within the changing pad and disposal container means.

* * * * *